(12) United States Patent
Domínguez Horta et al.

(10) Patent No.: US 8,324,164 B2
(45) Date of Patent: Dec. 4, 2012

(54) PEPTIDES AND ALTERED PEPTIDE LIGANDS DERIVED FROM HSP60 AND PHARMACEUTICAL COMPOSITIONS

(75) Inventors: Maria del Carmen Domínguez Horta, Ciudad de La Habana (CU); Gabriel Ramón Padrón Palomares, Ciudad de La Habana (CU); Nelia López Marin, Ciudad de La Habana (CU); Norailys Lorenzo Perez, Ciudad de La Habana (CU); Ariana Barberá Betancourt, Ciudad de La Habana (CU); Ariadna Hernández Garcia, Ciudad de La Habana (CU); Vivian Morera Cordova, Ciudad de La Habana (CU); Carelia Cosme Diaz, Ciudad de La Habana (CU); Nelson J. Merino Garcia, Ciudad de La Habana (CU); Ariel Vázquez Bonachea, Ciudad de La Habana (CU); José Suárez Alba, Ciudad de La Habana (CU)

(73) Assignee: Centro de Ingenieria Genetica Y Biotecnologia, Ciudad de La Habana (CU)

( * ) Notice: Subject to any disclaimer, the term of this patent is extended or adjusted under 35 U.S.C. 154(b) by 0 days.

(21) Appl. No.: 12/649,687

(22) Filed: Dec. 30, 2009

(65) Prior Publication Data

US 2010/0144642 A1 Jun. 10, 2010

Related U.S. Application Data

(62) Division of application No. 11/663,603, filed as application No. PCT/CU2005/000008 on Sep. 22, 2005.

(30) Foreign Application Priority Data

Sep. 24, 2004 (CU) .................... 2004-0207

(51) Int. Cl.
A61P 19/02 (2006.01)
A61P 29/00 (2006.01)
A61K 38/17 (2006.01)
C07K 14/47 (2006.01)

(52) U.S. Cl. ...................................... 514/16.6; 530/326

(58) Field of Classification Search ........................ None
See application file for complete search history.

(56) References Cited

U.S. PATENT DOCUMENTS

2002/0169302 A1* 11/2002 Havukkala et al. .......... 536/23.1

OTHER PUBLICATIONS

Dominguez et al. 2008. Biotecnologia Aplicada. 25: 230-235.Wells (1990) Biochemistry 29(37): 8509-8517.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*

* cited by examiner

*Primary Examiner* — Zachary Howard
(74) *Attorney, Agent, or Firm* — Hoffman & Baron, LLP

(57) ABSTRACT

Peptides of human heat shock protein of 60 kDa, that constitute epitopes for T cells, as well as their derived peptides, which are modified at the contact sites with the MHC molecule, are useful to induce mechanisms of peripheral tolerance, in particular mechanisms of anergy or mediated by clones of regulatory T cells in patients with Rheumatoid Arthritis. The invention also refers pharmaceutical compositions comprising such peptides for the treatment of Rheumatoid Arthritis.

4 Claims, 6 Drawing Sheets

PEPTIDES AND ALTERED PEPTIDE LIGANDS DERIVED FROM HSP60 AND PHARMACEUTICAL COMPOSITIONS

CROSS-REFERENCE TO RELATED APPLICATIONS

This application is a divisional of U.S. application Ser. No. 11/663,603 filed on Mar. 12, 2008, which is a U.S. National Phase Application of International Application No. PCT/CU05/00008 filed on Sep. 22, 2005, which asserts priority to Cuban Application No. CU2004/0207 filed on Sep. 24, 2004. The foregoing applications are hereby incorporated by reference in their entirety herein.

FIELD OF THE INVENTION

The present invention is related with peptides of human heat shock protein of 60 kDa (abbreviated hHsp60), and Altered Peptide Ligands (abbreviated APL) derived from them. Also, the invention is related with the pharmaceutical compositions comprising such peptides for the treatment of Rheumatoid Arthritis (RA).

BACKGROUND ART

The RA is an autoimmune disease of unknown etiology that affects approximately 1% of world's population. It is a syndrome characterized by chronic inflammation of the joints, although systemic manifestations can be also observed. This illness begins with the inflammation of the synovial membrane and frequently causes the erosive destruction of the adjacent cartilage and the bone, which result in moderate physical inability of 80% of the patients and an early mortality (Moctezuma, J. F. (2002) Manifestaciones articulares de la Artritis Reumatide. Revista Mexicana de Reumatología 17:211-219). RA can be presented at any age, without distinctions of races or ethnic groups, but the maximum incidence of its beginning happens between 25 and 55 years old. Among people with RA, the women overcome the men in a proportion from three to one (Emery, P. (2002) Early referral recommendation for newly diagnosed rheumatoid arthritis: evidence based development of to clinical guide. Ann Rheum Dis. 61:290-297).

The cause of RA is unknown. It is an illness that involves the presence of genetic, environmental, immunological and hormonal factors. Certain genes have a role in the immune system, associated with a tendency to develop RA. At the same time, some people with RA don't have these genes and other people having them never develop the illness. Therefore, it has been suggested that the genetic background is important but it is not decisive.

In models of autoimmune disease, microbial antigens with similar structure to own antigens can release a crossed response to autoantigens, producing an alteration in the mechanisms of tolerance and perpetuating an autoimmune response. In general sense, the damage and local necrosis in a tissue produced by an infectious agent could discover the autoantigen cryptic epitope, being able to activate autoreactivate T cells (Albert, L. J. (1999) Mechanisms of Disease: Molecular Mimicry and autoimmunity. N Engl J Med 341: 2068-2074)

The phase of transition of T lymphocyte between tolerance and immunity/autoimmunity is regulated at different levels. Two important parameters in this transition are the state of maturation of the Antigen Presenting Cells (abbreviated APC) and the levels of autoantigens that are detected by the immune system (Ohashi, P. S. (2002) Making and breaking tolerance. Current Opinion in Immunology 14:744-759).

One of the current hypotheses that tries to explain the development of autoimmune diseases, outlines that APC in absence of signs of the innate immune system or of signs of danger, remain relatively immature and induce tolerance in autoreactive T cells, when own peptides are presented to them (Steiman, R. M. (2000) The induction of tolerance by dendritic cells that have captured apoptotic cells. J Exp Med. 191:411-416). The induction of peripheral tolerance is also correlated with the concentration of own antigen (Kurts, C. (1999) CD8 T cell ignorance or tolerance to islet antigens depends on antigen dose. PNAS 96:12703-12707). An increment in the presentation of own antigens due to the increment of their expression levels, allows their detection by autoreactive ignorant T cells. If levels of own antigens are increased in absence of events that promote the maturation of APC, the tolerance to these antigens is maintained, otherwise, it happens in presence of proinflammatory signs or other events that promote the maturation of the APC, the tolerance is breaks by activation of the ignorant T cells and autoimmune diseases are developed (Janeway, C. A. (2002) Innate immune recognition. Annu Rev Immunol. 20:197-216). The infectious agents that have been object of study like cause of RA are: Epstein Bar virus, the retrovirus, virus of the hepatitis C, the *Mycobacterium tuberculosis* (abbreviated Mt) and the *Helicobacter pylori*, among others.

The pathogenesis of RA is characterized by the concerted action of different types of cells that cause the progressive destruction of the cartilage and the bone.

In normal situations a balance exists among the inflammatory cytokine as: TNFα, IL-1, IL-6, IL-15, IL-16, IL-17, IL-18 and the IFNγ, and the anti-inflammatory ones as IL-4, IL-11, IL-13 and antagonistic of IL-1 or TNFα. In the RA this balance moves however in favor of the inflammatory cytokines (Arend, W. P. (2001) Cytokine imbalance in the pathogenesis of rheumatoid arthritis: The role of interleukin-1 receiving antagonist. Semin Arthritis Rheum 30(2):1-6)

The recognition of an exogenous antigen or autoantigen is probably the reason of a series of events that cause destruction of the joints in patients with RA. This phenomenon cause the activation of T CD4+ lymphocytes that in cooperation with the stimulation of different cytokines, induces their differentiation to cells Th1 with the consequent liberation of proinflammatory cytokines (IL-2 and INFγ) (Simón, A. J. (2001) Biological therapy in Rheumatoid Arthritis. Magazine of Clinical Investigation 53(5):452-459). Many investigators coincide that the chronic inflammation of the joints is induced by these activated T cells that infiltrate the synovial membrane. The action of these cytokines on macrophages causes the production of high amount of TNFα and IL-1. These cause a series of local and systemic actions as regulating the expression of the molecules of adhesion in the endothelial cells (LFA1, ICAM-1), which recruit other cells to the inflammation sites. They also stimulate macrophages, fibroblasts, condrocytes and osteoclasts to the liberation of others mediators of the inflammation, as IL-15 and IL-8. TNFα and IL-1 stimulate the proliferation of the synovial membrane that causes formation of pannus, they can also induce the differentiation of B lymphocytes to cells producing antibodies that potentially participate in the destruction of the joint. They also inhibit the production of anti-inflammatory cytokines (IL-4 and IL-14) produced by Th2 cells and stimulate hepatocytes to liberate IL-6. IL-6 favors the production of the proteins of the acute phase, which participate strengthening the immune response (Forre, O. (2000) New possibilities of treatment in AR. Scand J Rheumatol 29(2):73-84).

Among autoantigens involved in the pathogenesis of RA is Hsp60, a protein that belongs to the family of the Hsp, which are immunogenic proteins with exceptionally evolutionary conservation. The immune response against the strange Hsp is an important mechanism of defense against bacterial infections. The antibodies against these proteins can be abundant in healthy people and in patient with autoimmune illnesses and they can cross react with the own antigens (Chen, W. (1999) Human 60-kDa Heat-Shock Protein: To Danger Signal to the Innate Immune System. J. Immunol. 162:3212-3219).

The Hsp65 of Mt is homologous to the Hsp60 of the mammals. This suggests that the Hsp60 can be recognized as autoantigen in patient with RA. Comparing patients with osteoarthritis and patients with RA, these last ones have an increase of proliferative response of B lymphocytes in the synovial liquid to the Hsp65 of mycobacterium. The intensity of the response correlates with the synovial inflammation. This response is not specific for RA compared with other inflammatory illnesses (Life, P. (1993) Responses to Gram negative enteric bacterial antigens by synovial T cells from patients with juvenile chronic arthritis: recognition of heat shock protein hsp60. J. Rheumatol. 20:1388-1396).

The concentration of Hsp is a possible sign of danger for the immune system, which are released from dead cells, and can induce an inflammatory response and to begin the maturation of the APC. The Hsp, are intracellular proteins, which are not expressed in the cellular membrane, neither are secreted, so that the Hsp are attractive candidates for molecules that constitute signs of danger (Van den Berg, WB. (1998): Joint inflammation and cartilage destruction may occur uncoupled. Springer Semin Immunopathol. 20:149-164).

Several preparations have been proposed using the Hsp60 or its derived peptides for the treatment of some autoimmune pathologies. For example in the patent EPO262710, the use of several peptides of the Hsp60 of Mt is proposed for the treatment and diagnosis of autoimmune illnesses, especially of arthritic conditions. This invention is based on the fact that previous infections with several bacteria can trigger the development of autoimmune illnesses, in genetically susceptible people, for example: patients with RA can show a high reactivity to microbial antigens.

These same inventors in the patent EPO322990 propose the use of others peptides of the Hsp60 of Mt with the same purpose of the previous patent.

In the patent application WO9610039 they intend the use of a peptide of the Hsp60 of Mt for the diagnosis and treatment of autoimmune arthritis.

In the patent application WO9711966, the authors intend the use of peptides of non conserved regions of the hHsp60, that don't coincide with the Hsp60 of bacteria that could induce tolerance in T cells of patients with RA.

The patent application WO0143691 proposes the use of pharmaceutical preparations composed specifically by peptides of the hHsp60 and their variants for the prevention of inflammatory illnesses such as RA.

In the U.S. Pat. No. 6,180,103 the authors intend the use of a peptide of the Hsp60 called p277 and its analogous for the diagnosis and prevention of the diabetes type I.

The U.S. Pat. No. 5,993,803 protects the use of the Hsp60, the peptide p277 and a group of derived peptides of this protein to reduce the severity of the immune response during the transplant of organs.

Recently it has been considered that the atherosclerosis presents a series of similar characteristics to autoimmune processes. In the patent application WO0072023 the authors purpose a method for the treatment and diagnosis of the atherosclerosis and coronary illnesses using a preparation that contains the protein Hsp60.

In the patent application WO02057795, a new method is protected for the diagnosis and treatment of the osteoporosis using proteins of the family of Hsp and proteins from pathogens such as: viruses and bacteria.

At the present time, cure doesn't exist for the RA. The current methods of treatment are centered in alleviating the pain, to reduce the inflammation, to retard the damages of the joints and to improve the functions and the well-being of the patients. Recently immunomodulating medications have been elaborated, that blocks cytokines that participate in the beginning and maintenance of the inflammatory response in RA, with the purpose to stop or slow the progression of the illness. For this kind of therapy two types of medications exist: blocking the action of the Tumor Necrosis Factor (abbreviated TNFα) and those that inhibit the action of the interleukin 1 (IL-1).

Although the results are promissory with the therapies anti-TNFα and anti-IL-1, the percentage of infections is high. Many of treated patients with these drugs develop serious infections that are fatal in some cases; including other autoimmune illnesses, neoplasias, etc. Besides, they are very expensive medications (Breshinan, B. (1998) Treatment of rheumatoid arthritis with recombinant human anti-interleukin-1 antagonist. Arthritis Reum. 41:2196-2204)

Oral tolerance has been proposed as a method of creating peripheral tolerance in front of certain antigens. This can be induced by mechanisms of active suppression, anergy or clonal deletion, depending on the doses and the frequency of the administration of the antigen. The method can induce regulatory T cells that are activated in a specific way by the antigen, but exert its action independently (active suppression). For the regulatory action takes place, it is not necessary to administer the supposedly pathogenic antigen, but any other able to induce the active suppression in the inflammatory focus, inhibiting the activity of the pathogenic effector cells. Collagen type II (abbreviated CII) is the autoantigen that has been used more frequently in this sense. The results of the studies carried out in patients with RA, using chicken and bovine CII have given contradictory results (Trentham, D. E. (1993) Effects of oral administration of type II collagen in rheumatoid arthritis. Science 261:1727-1730; Sieper, J. (1996) Oral type II collagen treatment in early rheumatoid arthritis: to double-blind, placebo-controlled, randomize trial. Arthritis Rheum. 39:41-51).

The U.S. Pat. No. 6,153,200 intends the use of a peptide of the Hsp70, protein belonging to the family of Hsp, to induce tolerance for oral route in patients with RA.

Another variant that has been suggested to induce tolerance is through APL peptides, based on the fact that T cells are activated if the specific T CD4+ lymphocytes for a certain antigenic peptide recognize the antigen presented by competent APC. Nevertheless, if the same T cell is first activated with a different form from the antigen, in which one of the contact sites with the TcR are lightly altered, it can result in a partial activation or even inactivation of the T cells. These antigens are named APLs. The APLs are similar to immunogenic peptides with one or several substitutions in the essential positions of contact with the TcR or with MHC that interfere the cascade of necessary events for the complete activation of the T cells.

Conceptually, APLs can be designed with similar properties to the immunogenic peptide (agonist) among other effects for increasing the response of T cells toward specific antigens. This effect is advantageous under pathological conditions as infectious illnesses. Peptides can also be designed with antagonistic properties to the immunogenic peptide that could be beneficial in the control of autoimmune illnesses since they can block the response of T cells acting as antagonistic of the TcR (M. De Magistris (1992) Antigen analog-major complex histocompatibility complexes act as antagonist of the T cell receptor. Cell 68:625-634), partial agonist or inducing a population of regulatory T cells that mediate the active suppression (Evavold, B. D. (1991) Separation of IL-4 production from Th cell proliferation by an altered T cell ligand. Science 252:1308-1310). The capacity to experimentally manipulate the intrinsic properties of peptide ligands allows altering the nature, the course and the power of the immune cellular response appropriately.

Up to this moment, two clinical trials in humans using type APL peptides have been performed for the treatment of autoimmune diseases. In both assays, the peptides are derived from an epitope in position 83 to 93 of the myelin basic protein. One of these trials included 142 patients with multiple sclerosis, and it was suspended because 9% of the patients developed hypersensitivity (Ludwig Kapposi (2000) Induction of non-encephalitogenic type 2 T helper-cell autoimmune response in multiple sclerosis after administration of an altered peptide ligand in to placebo controlled, randomized phase II trial. Nature Medicine 10:1176-1182).

The other trial included 25 patients and was also interrupted, because in three patients was observed an exacerbation of the illness (Bibiana Bielekova (2000) Encephalitogenic potential of the myelin basic protein peptide (amino acids 83-99) in multiple sclerosis: Results of to phase II clinical trial with an altered peptide ligand. Nature Medicine 6:1167-1175). The main author of this work analyzes the possible factors that determined these negative results, and outlines that the changes carried out in the APL's sites may originate new motifs of union to the HLA (like it happened in the case of the APL binding to DRB1*0404 present in patient I), the complex APL-HLA can also stimulate T cells not eliminated in the negative selection that can be cross-activated by the native autoantigen. In this trial high concentrations of the APL were used in the pharmaceutical preparations, which can stimulate T cells with high similarity for the autoantigen and to induce a heteroclitic T cells response. (Bibiana Bielekova and Roland Martin (2001) Antigen-specific immunomodulation via altered peptide tying. J Mol Med. 79:552-556).

For carrying out these two clinical trials, the authors didn't previously analyze the in vitro response of the T cells from the patients to the APL. They also did not consider the types of HLA molecules expressed by the treated patients The main challenge in the treatment of the autoimmune diseases is the development of therapeutic strategies that can eliminate pathogenic T cells with specificity, without affecting other non related T cells. Therefore, therapeutic search should find a secure, specific and effective way of turning off an advanced autoimmune process.

The present invention, in contrast to the state of the previous technique, proposes the use of peptides of the hHsp60 and its derived type APL, which induce inhibitory molecular mechanisms, in a specific way, of the course of RA.

SUMMARY OF THE INVENTION

The present invention solves the problem previously mentioned, providing peptides of the human protein of heat shock of 60 kDa that constitute epitopes for T cells, to induce mechanisms of tolerance, in particular anergy induction mechanisms or mediated by clones of regulatory T cells in patients with RA and that present the sequences:

```
E18-12
MGPKGRTVIIEQSWGSPKVTK          (SEQ. ID. NO: 1)

E18-3
SIDLKDKYKNIGAKLVQDVANNTNEEAG   (SEQ. ID. NO: 2)

F19-6
IIDPTKVVRTALLDAA               (SEQ. ID. NO: 3)
```

The patent application WO9711966, intends the use of peptides of the hHsp60 and of Mt based on the fact that they could induce tolerance in T cells and to prevent the RA. These authors corroborate certain improvement of the illness by administering these peptides to mice (Arthritis was previously induced with pristine). Contrary to this application, we have demonstrated that our peptides induce mechanisms of active suppression which induce peripheral tolerance in a very efficient way, corroborating a significant increase of IL-10 in two animal models of Arthritis, as well as in "ex vivo" assays using mononuclear cells of patients.

It is well known that fundamental response of T cells in the model of adjuvant-induced arthritis (AIA) is directed against the Hsp60. We checked in this model that our derived peptides of the hHsp60 exert a very marked therapeutic protection, producing an increase of the IL-10 and a decrease of TNFα levels. The same therapeutic effect exerted by these peptides, we have also checked in the animal model of collagen-induced arthritis (CIA), where the major response is against the type II collagen.

These facts indicate that therapeutic capacities of our peptides are independent of the induction agent and can mediate mechanisms of active suppression in the site of inflammation that could be extended to other autoantigens present in joints, which progressively contribute to the immunopathogenic process that takes place during the course of RA. These results reinforce the therapeutic possibilities of the use of our preparations for the treatment of RA.

These peptides are in particular useful, according to the present invention, for the design of derived type APL variants of the peptides E18-12 (SEQ. ID. NO: 1) and E18-3 (SEQ. ID. NO: 2), modified in the contact sites with the human MHC molecule and a derived type APL of the peptide F19-6 (SEQ. ID. NO: 3), modified in the contact sites with the rat MHC molecule. The respective sequences of amino acids are:

```
MGPKGRTVIIEQSWGSPKVTK    (SEQ. ID. NO: 1)
    1 2 34 56 7
``` it is substituted in the position 1 for: A, F, I, L, M, V, W, or Y
position 2 for: A, D, E, F, G, H, I, K, L, M, N, Q, R, S, T, V, W, or Y
position 3 for: A, K, V, R, T, I, P, L, N, S, G, Y, or M
position 4 for: A, D, E, F, G, H, I, K, L, M, N, Q, R, S, T, V, W, or Y
position 5 for: A, D, E, F, G, H, I, K, L, M, N, Q, R, S, T, V, or Y
position 6 for: A, D, E, F, G, H, I, K, L, M, N, P, Q, R, S, T, V, W, or Y
position 7 for: A, D, E, F, G, H, I, K, L, M, N, Q, R, S, T, V, or Y

```
SIDLKDKYKNIGAKLVQDVANNTNEEA    (SEQ ID. NO: 2)
      1  2 34 56 7   8
``` it is substituted in the position 1 for: L, I, V, M, Y, W, F, or A
position 2 for: A, D, E, F, G, H, I, K, L, M, N, Q, R, S, T, V, W, or Y position 3 for: A, F, I, K, L, M, P, R, S, T, V, W, or Y
position 4 for: L, I, V, M, Y, W, F, or A
position 5 for: A, D, E, F, G, H, I, K, L, M, N, Q, R, S, T, V, W, or Y
position 6 for: A, D, E, F, G, H, I, K, L, M, N, Q, R, S, T, V, W, or Y
position 7 for: A, F, I, K, L, M, P, R, S, T, V, W, or Y
position 8 for: A, D, E, F, G, H, I, K, L, M, N, Q, R, S, T, V, W, or Y

```
    IIDPTKVVRTALLDAA (F19-6)    (SEQ.ID. NO: 3)
        1    2
``` position 1 is substituted by H.
position 2 is substituted by E.

In a particular carrying out, derived type APL peptides have amino acid sequence selected from the group that consists of SEQ. ID. NO: 4, SEQ. ID. NO: 5, SEQ. ID. NO: 6, SEQ. ID. NO: 7, SEQ. ID. NO: 8, SEQ. ID. NO: 9, SEQ. ID. NO: 10, SEQ. ID. NO: 11, SEQ. ID. NO: 12, SEQ. ID. NO: 13, SEQ. ID. NO: 14, SEQ. ID. NO: 15, SEQ. ID. NO: 16, SEQ. ID. NO: 17, SEQ. ID. NO: 18, SEQ. ID. NO: 19, SEQ. ID. NO: 20 y SEQ. ID. NO: 21.

The peptides of the present invention can be produced by routine methods of peptide synthesis. The specific composition of each peptide can be assayed by the level and the quality of the immune response that it induces in experiments as those are described in the examples that will be presented later on.

All the sequences described above and in the examples are useful and can also be used as a base for the design and synthesis of derived peptides with improved properties.

The invention also includes pharmaceutical compositions that include one or more of previously enumerated peptides and optionally a pharmaceutically acceptable vehicle.

The administration of the pharmaceutical preparations to the patients will be in correspondence with the HLA class II molecules that are expressed by the specific patient.

The way of administration of the pharmaceutical compositions will depend on the cytokines pattern that these preparations induce in the "ex vivo" tests. The pharmaceutical preparations containing APL peptides inducing a regulatory response will be administered by intradermal or subcutaneous route. The pharmaceutical preparations containing the original peptides inducing a TH1 response will be able to be administered by oral route.

The amounts of peptides in the pharmaceutical compositions of this invention are those that produce an effective immune response in the host. The effective amount is the quantity that when is administered induces molecular mechanisms that significantly diminish the inflammatory signs characteristic of the RA and stop the damages in the joints characteristic of the course of this illness. The amount of the pharmaceutical composition administered to the host can also vary depending on of several factors that include: the used peptides, ACR score (American College of Rheumatology, abbreviated ACR), HLA type II, time of having diagnosed the illness, age, sex, general health, as well as the level of immunological response in general.

The present invention also relates a method of treatment of the RA, which includes the administration to a patient of effective amounts of peptides or the pharmaceutical compositions referred previously.

BRIEF DESCRIPTION OF THE DRAWINGS

In part, results are shown graphically in the following figures.

DETAILED DESCRIPTION OF PARTICULAR EMBODIMENTS/EXAMPLES

Example 1

Figure 1:
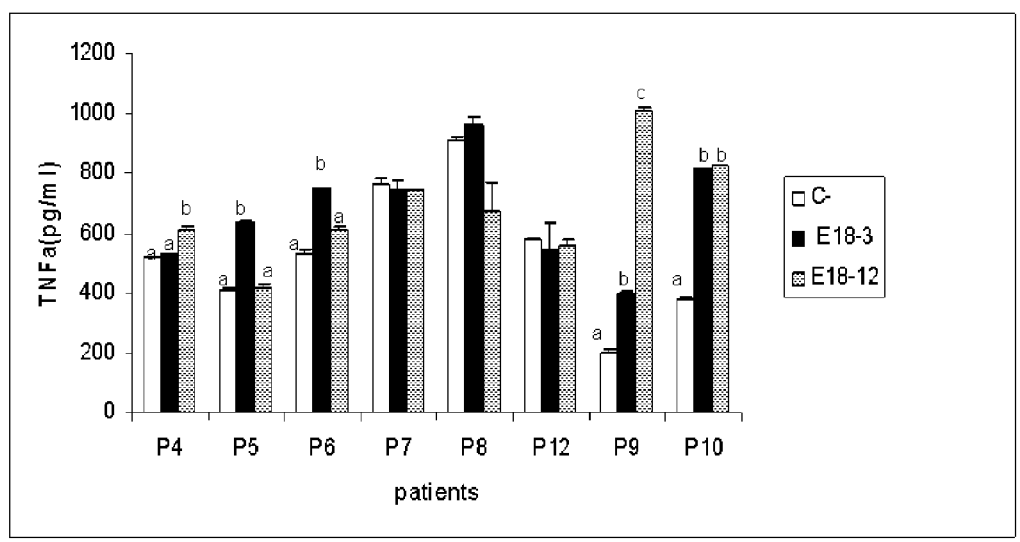
FIG. 1: TNFα levels induced by E18-3 and E18-12 peptides in PBMC (peripheral blood mononuclear cells) from patients with Rheumatoid Arthritis (RA). PBMC from RA patients were stimulated with 40 µg/ml of E18-12 or E18-3 peptide during 24 hours, and cytokine concentration was determined in the supernatant by ELISA kits. Different letters (a or b or c) represent the existence of statistically significant differences. C-: PBMC without peptide as control.

Peptides of the hHsp60 Presented by Human HLA

The selected peptides of the hHsp60 were those reported as epitopes of human T cells by the used programs: SYFPEITHI (Hans-Georg Rammensee, Jutta Bachmann, Niels Nikolaus Emmerich, Oskar Alexander Bachor and Stefan Stevanovic. 1999. Immunogenetics 50:213-219. SYFPEITHI: database for MHC ligands and peptide motifs. ProPred (Singh, H. and Raghava, G. P. S. 2001. ProPred: Prediction of HLA-DR binding sites. Bioinformatics, 17(12):1236-37).

The sequences corresponding to these peptides are shown in Table 1.

TABLE 1

Sequence of hHsp60 peptides presented by human HLA.

| Peptides | Position in the sequence | Amino acid Sequence |
|---|---|---|
| E18-12 | 55-75 | MGPKGRTVIIEQSWGSPKVTK (SEQ. ID. NO: 1) |
| E18-3 | 83-110 | SIDLKDKYKNIGAKLVQDVANNTNEEAG (SEQ. ID. NO: 2) |

Example 2

Design of APL with Modifications in the Amino Acids Involved in the Binding to the MHC Starting from the peptides selected in example 1, we have modified the positions involved in the binding to the specific MHC (positions 1, 3, 4, 6, 8 or 9) trying to increase the affinity of the peptide for the HLA molecule. It was searched for the optimal residuals in each one of these positions that could be anchorage residuals if the peptide was selected for methods that use binding motifs (SYFPEITHI) or residuals able to increase the score of the peptide as MHC ligand if the selection of the peptide was made using another algorithm type (ProPred).

As a result of these analyses, the peptide E18-12 has been substituted in the positions 1 to 7 by each one of the amino acids that are specified as follow:

```
MGPKGRTVIIEQSWGSPKVTK      (SEQ. ID. NO: 1)
1  2 34 56 7
``` it is substituted in the position 1 for: A, F, I, L, M, V, W, or Y
position 2 for: A, D, E, F, G, H, I, K, L, M, N, Q, R, S, T, V, W, or Y
position 3 for: A, K, V, R, T, I, P, L, N, S, G, Y, or M
position 4 for: A, D, E, F, G, H, I, K, L, M, N, Q, R, S, T, V, W, or Y
position 5 for: A, D, E, F, G, H, I, K, L, M, N, Q, R, S, T, V, or Y
position 6 for: A, D, E, F, G, H, I, K, L, M, N, P, Q, R, S, T, V, W, or Y
position 7 for: A, D, E, F, G, H, I, K, L, M, N, Q, R, S, T, V, or Y

```
SIDLKDKYKNIGAKLVQDVANNTNEEAG    (SEQ. ID. NO: 2)
   1  2 3 45 6 7    8
``` it is substituted in the position 1 for L, I, V, M, Y, W, F, or A
position 2 for A, D, E, F, G, H, I, K, L, M, N, Q, R, S, T, V, W, or Y
position 3 for A, F, I, K, L, M, P, R, S, T, V, W, or Y
position 4 for L, I, V, M, Y, W, F, or A
position 5 for A, D, E, F, G, H, I, K, L, M, N, Q, R, S, T, V, W, or Y
position 6 for A, D, E, F, G, H, I, K, L, M, N, Q, R, S, T, V, W, or Y
position 7 for A, F, I, K, L, M, P, R, S, T, V, W, or Y
position 8 for A, D, E, F, G, H, I, K, L, M, N, Q, R, S, T, V, W, or Y

Example 3

Cytokines Measurement in Patients with RA Induced by E18-12 and E18-3 Peptides Assays for cytokines measurement using blood of patients with RA were carried out: TNFα, IFNδ and IL-10. The potentiality of the peptides of the hHsp60 to increase or to diminish the different cytokines involved in the pathogenesis of the illness was evaluated in these assays.

Ten mL of blood were extracted from each patient, which were diluted ½ in PBS 1×. It was added 5 mL of this dilution to 3 mL of Ficoll-Paque (Amershan) in centrifugation tubes of 15 mL, and centrifuged during 30 min at 1200 rpm. The ring corresponding to mononuclear cells was extracted. Later, the cells were washed twice with 15 mL of PBS 1× and after each washing they were centrifuged at 900 rpm. Finally, the precipitate was resuspended in RPMI 1640 medium containing 10% of bovine fetal serum supplemented with penicillin (100 U/mL), streptomycin (100 ig/mL), 25 HEPES mM/L and L-glutamine 2 mM (all acquired of Gibco BRL).

The mononuclear cells obtained were seeded in a number of $10^6$ cells/well in plates of 24 wells (Costar) in a volume of 800 µL. Afterwards, the peptides of the hHsp60 were added in a concentration range from 0.5 µg/ml up to 100 µg/ml, in order to know the optimal concentration of each peptide to modulate the cytokine levels. The Phytohemagglutinin (PHA) to 1% it was used as positive control of cell stimulation, while the RPMI 1640 alone was used as control of the basal cell growth.

The cells were cultured during 24 hours and later on, the supernatant of each well was taken, diluted ½, and cytokine concentration was determined by specific kits (Quantikine®, R&D Systems) according to the recommendations of the suppliers.

The levels of TNFα modulated by the E18-3 and E18-12 peptides in mononuclear cells of patients with RA are represented in FIG. 1. Patients represented by P4, P5 and P16 express the molecule DR 0306, the patients identified as P7, P8 and P12 express the molecule DR 0303, while patient P9 presents a genotype DR0506 and patient P10 has a genotype DR 0204. In this figure, the letter A represents the cultured cells in vitro without peptides; while B corresponds to the cells stimulated in vitro with E18-3 peptide and C represents cells stimulated in vitro with E18-12 peptide.

In the figure when exists statistically significant difference among the levels of the cytokines secreted by the cells stimulated with the peptides with respect to non stimulated cells, a different letter is assigned in the bars for levels of the corresponding cytokine.

As it is observed in FIG. 1, the induction of the synthesis of TNFα in mononuclear cells of patients, stimulated with E18-12 and E18-3 peptides depends on the HLA type II molecules that these patients express. In patients P4, P5 and P6 that present a genotype DR 0306, a statistically significant increment of the concentration of TNFα was observed, in comparison with the cells not stimulated with peptides.

This same effect takes place in the patient P9 of genotype DR 0506 and the patient P10 DR 0204.

In patients P7, P8 and P12 presenting a genotype DR 0303, any difference in levels of TNFα was not observed, when mononuclear cells are stimulated with our peptides.

The modulation of IL-10 levels for E18-3 and E18-12 peptides are represented in FIG. 1, where the letter A represents cultured cells in vitro without peptides; while B corresponds to cells stimulated in vitro with the E18-3 peptide and C represents cells stimulated in vitro with E18-12 peptide.

Figure 2:
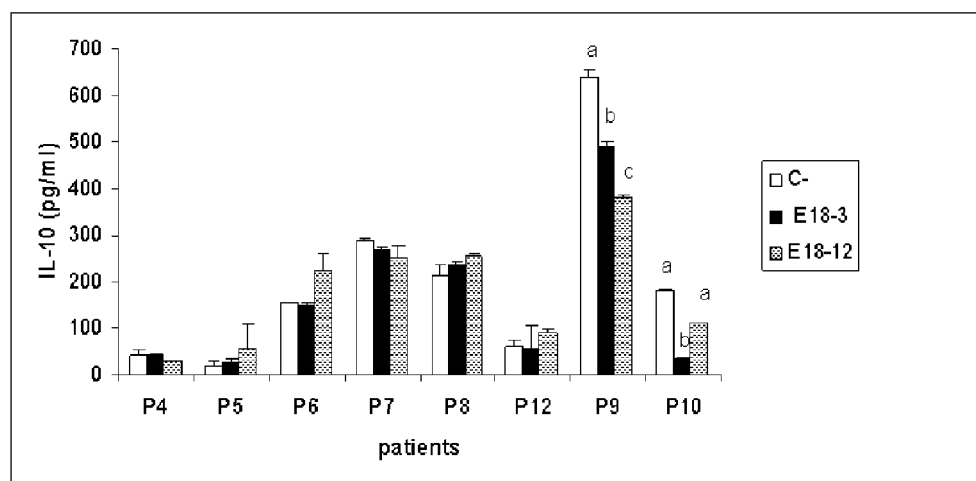
FIG. 2: IL-10 levels induced by E18-3 and E18-12 peptides in PBMC (peripheral blood mononuclear cells) from patients with Rheumatoid Arthritis (RA). PBMC from RA patients were stimulated with 40 µg/ml of E18-12 or E18-3 peptide during 24 hours, and cytokine concentration was determined in the supernatant by ELISA kits. Different letters (a or b or c) represent the existence of statistically significant differences. C-: PBMC without peptide as control.

In the case of IL-10, as it is observed in FIG. 2, there is a significant decrease of this cytokine in the patients P9 and P10, but in the rest of the patients were not significant changes.

From these observations we can infer that E18-12 and E18-3 peptides induce a TH1 phenotype in peripheral mononuclear cells.

A therapeutic variant of original peptides: E18-12 or E18-3 could be their administration by oral route, so they will induce mechanisms of tolerance that contributed significantly to decrease the inflammation.

Example 4

Cytokine Measurement in Patients with RA Induced by Derived Type APL Peptides

From previous results, we decided to modify these original peptides corresponding to epitopes of T cells, at the sites of contact with HLA molecule, using Bioinformatic tools, so that the modified type APL peptides would be able to change the pattern of cytokines to a regulating phenotype. In addition, modifications made in each of these peptides fulfill with peptide binding motifs reported for most of the HLA molecules expressed by the patients that theoretically will favor the interaction of each of them with different HLA molecules.

Assays for measurement of the cytokines: TNFα and IL-10, were carry out using blood of patients with RA. The potentiality of derived type APL peptides from the hHsp60 to increase or to diminish the different cytokines involved in the pathogenesis of the disease was evaluated in these tests. In addition, the original peptides were included in this evaluation (E18-3, E18-12) as experimental controls.

The APL peptides evaluated in these tests were the following:

| | |
|---|---|
| MGPKGRTVIILQSWGSPKVTK | (SEQ. ID. NO: 5) |
| MGPKGRTVIIMQSWGSPKVTK | (SEQ. ID. NO: 6) |
| MGPKGRTVIIAQSWGSPKVTK | (SEQ. ID. NO: 7) |
| MGPKGRTVIIEQSLGSPKVTK | (SEQ. ID. NO: 8) |
| MGPKGRTVIIEQSMGSPKVTK | (SEQ. ID. NO: 9) |
| MGPKGRTVIILQSLGSPKVTK | (SEQ. ID. NO: 10) |
| MGPKGRTVIILQSMGSPKVTK | (SEQ. ID. NO: 11) |
| MGPKLRTVIIEQSWGSPKVTK | (SEQ. ID. NO: 12) |
| MGPKLRTVIILQSMGSPKVTK | (SEQ. ID. NO: 13) |
| SIDLKDKLKNIGAKLVQDVANNTNEEA | (SEQ. ID. NO: 14) |
| SIDLKDKYKNIGAKLSQDVANNTNEEA | (SEQ. ID. NO: 15) |
| SIDLKDKLKNIGAKLSQDVANNTNEEA | (SEQ. ID. NO: 16) |
| SIDLKDKYKNAGAKLVQDVANNTNEEA | (SEQ. ID. NO: 17) |
| SIDLKDKYKNIGAKLVQLVANNTNEEA | (SEQ. ID. NO: 18) |
| SIDLKDKYKNIGAKLVQAVANNTNEEA | (SEQ. ID. NO: 19) |
| SIDLKDKYKNIGAKLVQDVANNANEEA | (SEQ. ID. NO: 20) |
| SIDLKDKYKNIGAKLVQLVANNANEEA | (SEQ. ID. NO: 21) |

Ten mL of blood were extracted from each patient and diluted ½ in PBS 1×. It was added 5 mL of this dilution to 3 mL of Ficoll-Paque (Amershan) in centrifugation tubes of 15 mL, and centrifuged during 30 min at 1200 rpm. The ring corresponding to mononuclear cells was extracted. Later, the cells were washed twice with 15 mL of PBS 1× and after each washing they were centrifuged at 900 rpm. Finally, the precipitate was resuspended in RPMI 1640 medium containing 10% of bovine fetal serum supplemented with penicillin (100 U/mL), streptomycin (100 μg/mL), 25 HEPES mM/L and L-glutamine 2 mM (all acquired of Gibco BRL).

Obtained mononuclear cells were cultured in number of $10^6$ cells/well in plates of 24 wells (Costar) in a volume of 800 μL. Cells were stimulated with peptides [E18-3, E18-12, E18-3APL1 (SEQ. ID. NO: 18), E18-3APL2 (SEQ. ID. NO: 21), E18-12APL1 (SEQ. ID. NO: 5), E18-12APL3 (SEQ. ID. NO: 12)] at a concentration of 40 μg/mL and by triplicate. RPMI 1640 was used as control of the basal cellular growth.

Cells were cultured during 24 hours and later supernatants of each well were taken, diluted ½ and the concentration of cytokines were determined by specific kits (Quantikine®, R&D Systems) according to the recommendations of the suppliers.

Figure 3:
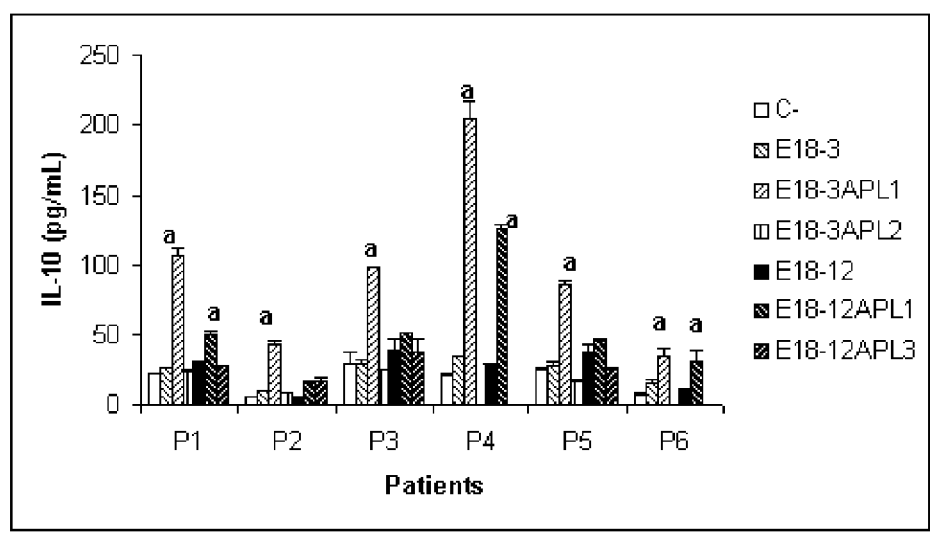
FIG. 3: IL-10 levels induced by APL derived from E18-3 and E18-12 in PBMC (peripheral blood mononuclear cells) from patients with Rheumatoid Arthritis (RA). PBMC from RA patients were stimulated with 40 µg/ml of corresponding peptide during 24 hours, and cytokine concentration was determined in the supernatant by ELISA kits. Different letters (a or b or c) represent the existence of statistically significant differences. C-: PBMC without peptide as control.

In FIG. 3 is shown the levels of IL-10 induced by original peptides (E18-12 and E18-3) and a peptide panel of APLs: E18-3APL1 (SEQ. ID. NO: 18); E18-3APL2 (SEQ. ID. NO: 21); E18-12APL1 (SEQ. ID. NO: 5); E18-12APL3 (SEQ. ID. NO: 12). In this figure, the letters indicate statistically significant differences (we only refer statistical significance between the different peptides and control cells in each patient individually). In addition, cells of patients P4 and P6 were not stimulated by peptides E18-3APL2 nor E18-12APL3. It is evident that, in all patients, peptide E18-3APL1 increases the levels of IL-10 very significantly with respect to the non stimulated cells. The increase induced by this peptide in some of the patients, as P2 and P4, was about 9 times higher than the amount produced by the cells without stimulation, and in patients as P1, P3 and P5 about 5 times superior. Also, similar results were obtained with E18-12APL1 due to a significant increase in levels of IL-10 in patients P1, P4 and P6. On the other hand, neither the original peptides nor peptides E18-3APL2 and E18-12APL3 induced an increase in the levels of IL-10 in comparison with the cells that represent the negative control.

Figure 4:
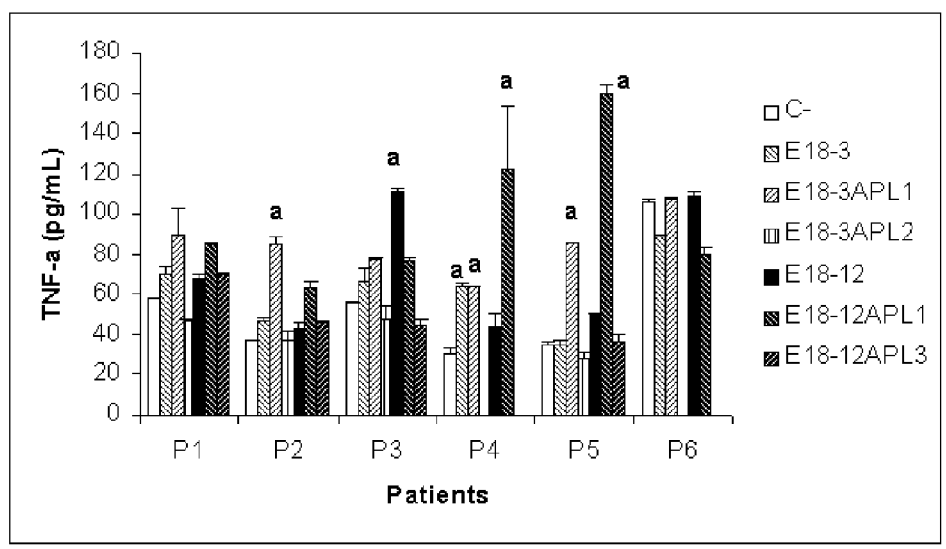
FIG. 4: TNFα levels induced by APL derived from E18-3 and E18-12 peptides in PBMC (peripheral blood mononuclear cells) from patients with Rheumatoid Arthritis (RA). PBMC from RA patients were stimulated with 40 µg/ml of corresponding peptide during 24 hours, and cytokine concentration was determined in the supernatant by ELISA kits. Different letters (a or b) represent the existence of statistically significant differences. C-: PBMC without peptide as control.

In FIG. 4 is shown the levels of TNFα induced by different peptides in the same group of patients. In this figure, the letters indicate statistically significant differences (we only refer statistical significance between different peptides and control cells in each patient individually). In addition, cells of patients P4 and P6 were not stimulated by peptides E18-3APL2 nor E18-12APL3). As it can be appraised, all the patients do not respond with the same intensity to the stimulus with different peptides, although it is notorious that the response was quite homogenous. On the other hand, the peptide that increased more the production of TNFα was the E18-12APL1, mainly in patients P4 and P5, whereas patients: P1, P2 and P3 showed a slight increase with respect to the negative control. Also, peptide E18-3APL1 had a similar behavior in most of the patients. In the case of peptide E18-3APL1 the cells of the patients P2, P4 and P5, showed the major increase of the levels of TNFα, although was less marked. In this test, we obtained similar results to previous evaluations with the original peptides. The previous results indicate that neither peptide nor its APL induce a decrease of TNFα expression in mononuclear cells of the patients.

Figure 5:
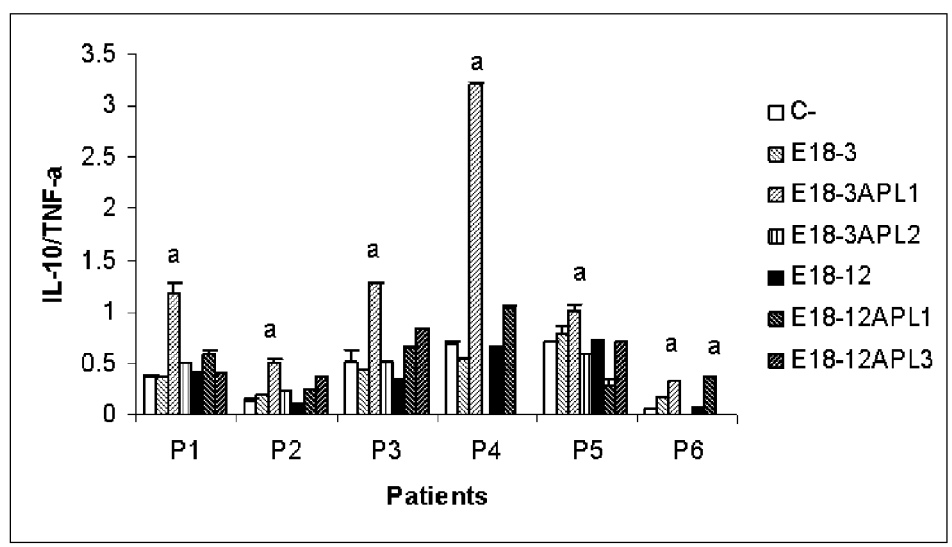
FIG. 5: Ratio of the net increment of IL-10 levels and the net increment of TNF-α levels induced by peptides in the PBMC (peripheral blood mononuclear cells) from RA patients. Different letters (a or b) represent the existence of statistically significant differences. C-: PBMC without peptide as control.

These results could be contradictory, since such APLs that increase the production of IL-10 promote an increase in the levels of TNFα. In FIG. 5 is shown ratio of the levels of IL-10 and TNFα induced by original peptides and their APLs. In this figure, the letters indicate statistically significant differences (we only refer statistical significance between different peptides and control cells in each patient individually). In addition, cells of patients P4 and P6 were not stimulated by peptides E18-3APL2 nor E18-12APL3). It is evident the fact that the increase of IL-10 with respect to TNFα levels was considerably higher, because the cells stimulated with the E18-3APL1 showed an index higher than 1 in four out of six patients, which indicates that IL-10 levels exceeded to those of TNFα. In addition, in all patients, IL-10 levels were considerably higher in cells stimulated with peptide E18-3APL1 with respect to cells that constituted the negative control, showing statistically significant differences. In the case of the E18-12APL1 the differences in comparison to the negative control were not so remarkable. So, although E18-3APL1 increases the levels of TNFα, the net predominant effect is the increase in the levels of IL-10, which is translated in a polarization of the response in favor of immunosuppressor cytokines.

The results of the study are extremely promissory, because it suggested that these two APLs could be administered to patients and could induce a subpopulation of regulatory T cells secretory of IL-10 that mediate an active suppression at systemic level. Another partial conclusion that we can arrive by means of the analysis of these results, is that these APLs practically display a homogenous behavior in all the studied patients, independently of the genotype that they have. These results are extremely encouraging, because it would allow that the administration of these APL had the same effect in all the patients, in spite of the existing differences with respect to the type of HLA-II molecules that they have.

From our experimental results, the fundamental advantage of the present invention is the use of pharmaceutical preparations containing immunomodulating peptides of the human stress protein Hsp60, corresponding to T cell epitopes of or variants type APL of these peptides, that can be effectively used in the treatment of patients with RA, inducing a specific immune response directed to silence the clones of involved autorreactive T cells in the immunopathogenic mechanisms of this disease.

The treatment we propose in this invention is reasonable and can be extended to a large number of patients and also it can be used in combination with current therapies for this disease.

Example 5

Evaluation of the Therapeutic Effect of Derived Type APL Peptides, in an Animal Model where Arthritis is Induced with Mt The animals were separated in twelve groups of eight rats each one. The disease was induced in eleven animal groups (Group I-Group XI), ten of them were treated with peptides and one stayed as control of the induction of the disease. Animal groups that were treated with peptides, received 50 µg of peptide by rat in a volume of 100 µL of PBS, days 12, 14, 16, 18, 20, 22, 24, 26 after induction of the disease with Mt.

The separated animals in twelve groups were treated with the following form:

Group I: received peptide E18-12 (SEQ. ID. NO: 1)
Group II: received peptide corresponding to: SEQ. ID. NO: 5
Group III: received peptide corresponding to: SEQ. ID. NO: 8
Group IV: received peptide corresponding to: SEQ. ID. NO: 12
Group V: received peptide corresponding to: SEQ. ID. NO: 13
Group VI: received peptide E18-3 (SEQ. ID. NO: 2)
Group VII: received peptide corresponding to: SEQ. ID. NO: 14
Group VIII: received peptide corresponding to: SEQ. ID. NO: 15
Group IX: received peptide corresponding to: SEQ. ID. NO: 16
Group X: received peptide corresponding to: SEQ. ID. NO: 17
Group XI: do not received peptide (control of disease induction)
Group XII: the disease was not induced or administered any peptide (negative control).

Days 21 and 35 after the induction, several animals from each group were sacrificed, spleens were extracted and sample was taken from joints for histopathological analysis.

In the groups of animals treated with peptides type APL, the clinical improvement was significant in comparison with the non treated animal group and with the groups treated with E18-12 and E18-3. These results were corroborated by histopathological analysis and by measurement of cytokines, demonstrating in all cases a superiority of derived type APL peptides upon original peptides.

Figure 6:
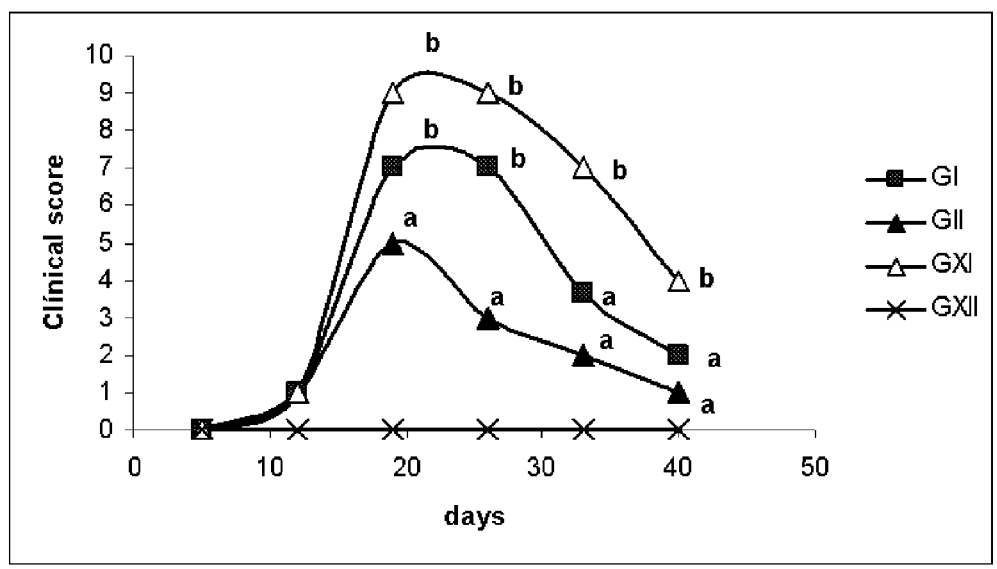
FIG. 6: Evaluation of the clinical signs of Arthritis in rats treated with SEQ. ID. NO: 1 and SEQ. ID. NO: 5 peptides by intradermal route, in AIA model. Arthritis was induced on day 0 by immunization with heat-killed Mycobacterium tuberculosis (MT) in Incomplete Freund Adjuvant. On day 10, rats were randomly divided into five groups: Group I (GI): rats inoculated with wild peptide E18-12 (SEQ. ID. NO: 1), Group II (GII): rats inoculated with peptide corresponding to: SEQ. ID. NO: 5, Group XI (GXI): non-treated rats, Group XII (GXII): healthy rats. Different letters (a or b) represent the existence of statistically significant differences.

In FIG. 6 we show the graphic of evolution of the disease in four animal groups pertaining to this animal model. In this case, the groups are: group I (animals treated with E18-12), group II (animals treated with E18-12APL1 SEQ. ID. NO: 5), group XI (control of the disease induction) and group XII (healthy animals). In this graph, different letters indicate significant differences (p<0.001) (it refers to the statistical significant between all groups in measured specific days.

It is possible to appreciate in this graph, that from day 12 after the induction of the disease, the animals of groups I, II and XI began to show the characteristic clinical signs of RA. Many animals also presented extra-articular manifestations like nodules in the ears, in the tail and in the extremities. The most severe manifestations of the RA were observed around day 20 for the three ill animal groups. In the case of animals treated with E18-12, in day 21 we could not appreciate significant differences with respect to the control of the disease induction group. Nevertheless, around day 35 after the induction of the disease, clinical signs in animals of this group were significantly inferior to those of group XI (p<0.001). These results indicate that protective effect of the E18-12 peptide is shown around day 35. In this sense, it would be recommendable to administer this peptide in earlier phases of the disease in order to obtain better results at day 21. However, in the case of animals of groups II the clinical signs of inflammation were evidently smaller in comparison with groups I and XI (p<0.001), which indicates that this peptide exerts a potent protective effect in the animals where the disease was induced.

INCORPORATION OF SEQUENCE LISTING

Incorporated herein by reference in its entirety is the Sequence Listing for the application. The Sequence Listing is disclosed on a computer-readable ASCII text file and created on Jun. 24, 2011. The sequence.txt file is 8.0 kb in size.

The invention claimed is:

1. A peptide consisting of SEQ ID NO: 1.

2. A pharmaceutical composition comprising the peptide of claim 1 and a pharmaceutically acceptable vehicle.

3. A peptide consisting of SEQ ID NO: 5.

4. A pharmaceutical composition comprising the peptide of claim 3 and a pharmaceutically acceptable vehicle.

* * * * *

SEQUENCE LISTING

<160> NUMBER OF SEQ ID NOS: 21

<210> SEQ ID NO 1
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 1

Met Gly Pro Lys Gly Arg Thr Val Ile Ile Glu Gln Ser Trp Gly Ser
1               5                   10                  15

Pro Lys Val Thr Lys
            20

<210> SEQ ID NO 2
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 2

Ser Ile Asp Leu Lys Asp Lys Tyr Lys Asn Ile Gly Ala Lys Leu Val
1               5                   10                  15

Gln Asp Val Ala Asn Asn Thr Asn Glu Glu Ala Gly
            20                  25

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 3

Ile Ile Asp Pro Thr Lys Val Val Arg Thr Ala Leu Leu Asp Ala Ala
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 4

Ile Ile Asp Pro Thr Lys Val Val Arg Thr Ala Leu Leu Asp Ala Ala
1               5                   10                  15

<210> SEQ ID NO 5
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 5

Met Gly Pro Lys Gly Arg Thr Val Ile Ile Leu Gln Ser Trp Gly Ser
1               5                   10                  15

Pro Lys Val Thr Lys
            20

<210> SEQ ID NO 6

```
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 6

Met Gly Pro Lys Gly Arg Thr Val Ile Ile Met Gln Ser Trp Gly Ser
1               5                   10                  15

Pro Lys Val Thr Lys
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 7

Met Gly Pro Lys Gly Arg Thr Val Ile Ile Ala Gln Ser Trp Gly Ser
1               5                   10                  15

Pro Lys Val Thr Lys
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 8

Met Gly Pro Lys Gly Arg Thr Val Ile Ile Glu Gln Ser Leu Gly Ser
1               5                   10                  15

Pro Lys Val Thr Lys
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 9

Met Gly Pro Lys Gly Arg Thr Val Ile Ile Glu Gln Ser Met Gly Ser
1               5                   10                  15

Pro Lys Val Thr Lys
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Met Gly Pro Lys Gly Arg Thr Val Ile Ile Leu Gln Ser Leu Gly Ser
1               5                   10                  15

Pro Lys Val Thr Lys
            20

<210> SEQ ID NO 11
```

<211> LENGTH: 21
<212> TYPE: PRT
<213> ORGANISM: Artificial Sequence
<220> FEATURE:
<223> OTHER INFORMATION: Synthetic Peptide

<400> SEQUENCE: 11

Met Gly Pro Lys Gly Arg Thr Val Ile Ile Leu Gln Ser Met Gly Ser
1               5                   10                  15

Pro Lys Val Thr Lys
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 12

Met Gly Pro Lys Leu Arg Thr Val Ile Ile Glu Gln Ser Trp Gly Ser
1               5                   10                  15

Pro Lys Val Thr Lys
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 13

Met Gly Pro Lys Leu Arg Thr Val Ile Ile Leu Gln Ser Met Gly Ser
1               5                   10                  15

Pro Lys Val Thr Lys
            20

<210> SEQ ID NO 14
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 14

Ser Ile Asp Leu Lys Asp Lys Leu Lys Asn Ile Gly Ala Lys Leu Val
1               5                   10                  15

Gln Asp Val Ala Asn Asn Thr Asn Glu Glu Ala
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 15

Ser Ile Asp Leu Lys Asp Lys Tyr Lys Asn Ile Gly Ala Lys Leu Ser
1               5                   10                  15

Gln Asp Val Ala Asn Asn Thr Asn Glu Glu Ala
            20                  25

<210> SEQ ID NO 16

```
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 16

Ser Ile Asp Leu Lys Asp Lys Leu Lys Asn Ile Gly Ala Lys Leu Ser
1               5                   10                  15

Gln Asp Val Ala Asn Asn Thr Asn Glu Glu Ala
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 17

Ser Ile Asp Leu Lys Asp Lys Tyr Lys Asn Ala Gly Ala Lys Leu Val
1               5                   10                  15

Gln Asp Val Ala Asn Asn Thr Asn Glu Glu Ala
            20                  25

<210> SEQ ID NO 18
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 18

Ser Ile Asp Leu Lys Asp Lys Tyr Lys Asn Ile Gly Ala Lys Leu Val
1               5                   10                  15

Gln Leu Val Ala Asn Asn Thr Asn Glu Glu Ala
            20                  25

<210> SEQ ID NO 19
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 19

Ser Ile Asp Leu Lys Asp Lys Tyr Lys Asn Ile Gly Ala Lys Leu Val
1               5                   10                  15

Gln Ala Val Ala Asn Asn Thr Asn Glu Glu Ala
            20                  25

<210> SEQ ID NO 20
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 20

Ser Ile Asp Leu Lys Asp Lys Tyr Lys Asn Ile Gly Ala Lys Leu Val
1               5                   10                  15

Gln Asp Val Ala Asn Asn Ala Asn Glu Glu Ala
            20                  25

<210> SEQ ID NO 21
```

```
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 21

Ser Ile Asp Leu Lys Asp Lys Tyr Lys Asn Ile Gly Ala Lys Leu Val
1               5                   10                  15

Gln Leu Val Ala Asn Asn Ala Asn Glu Glu Ala
            20                  25
```